United States Patent
Davis et al.

(10) Patent No.: US 6,391,260 B1
(45) Date of Patent: *May 21, 2002

(54) INSTRUMENT POUCH FOR STERILIZATION PROCESS AND METHOD OF STERILIZING AN ARTICLE

(75) Inventors: Phillip Davis, Weston; Vito L. Dipinto, South Windsor, both of CT (US)

(73) Assignee: General Hospital Supply Corporation, Wilton, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/256,458

(22) Filed: Feb. 23, 1999

Related U.S. Application Data

(63) Continuation-in-part of application No. 09/148,121, filed on Sep. 4, 1998, now Pat. No. 6,248,293.

(51) Int. Cl.[7] ................................................. A61L 2/20
(52) U.S. Cl. .......................... 422/28; 422/300; 206/370; 206/438; 229/69
(58) Field of Search ................................. 422/292, 297, 422/300, 22, 23, 28; 206/370, 523, 557, 438; 428/159; 229/69

(56) References Cited

U.S. PATENT DOCUMENTS

| | | |
|---|---|---|
| 4,142,632 A | 3/1979 | Sandel |
| D263,076 S | 2/1982 | Sandel |
| D263,745 S | 4/1982 | Sandel |
| 4,385,692 A * | 5/1983 | Eldridge, Jr. |
| 4,485,919 A | 12/1984 | Sandel |
| 4,671,943 A | 6/1987 | Wahlquist |
| 4,798,292 A | 1/1989 | Hauze |
| 5,098,676 A | 3/1992 | Brooks, Jr. |
| 5,325,987 A | 7/1994 | Alpern et al. |
| 5,340,551 A | 8/1994 | Berry, Jr. |
| 5,389,084 A | 2/1995 | Horan et al. |
| 5,407,648 A | 4/1995 | Allen et al. |
| 5,518,115 A | 5/1996 | Latulippe |
| 5,595,296 A | 1/1997 | Wood |
| 5,667,753 A | 9/1997 | Jacobs et al. |
| 5,792,422 A * | 8/1998 | Lin et al. ..................... 422/300 |

OTHER PUBLICATIONS

Dec., 1997, Feldman et al., Compatability of Medical Devices . ., Medical Devices and Diagnostic Industry.

1998 Brochure for Sterad Sterilization System, Advanced Sterilization Products (7 pages).

(List continued on next page.)

Primary Examiner—Elizabeth McKane
(74) Attorney, Agent, or Firm—Law Office of Roger C. Phillips

(57) ABSTRACT

A method for sterilizing an article in a sterilization unit, the method including placing the article within a foam plastic instrument pouch having a closed cell construction, and positioning the closed cell foam plastic instrument pouch containing the article within the sterilization unit. The sterilization unit is then operated such that the article within the instrument pouch is sterilized, whereby the instrument pouch containing the article is removed from the sterilization unit. An instrument pouch for containing and protecting an article during sterilization is also provided. The pouch includes a foam plastic backing sheet for lining a base of a tray, the base having a multiplicity of holes, and a foam plastic pocket secured to the backing sheet such that at least a portion of an article can be received between the pocket and the backing sheet. The pouch has a multiplicity of holes arranged such that at least a portion of the holes of the pouch will be generally aligned with at least a portion of the holes of the base of the tray. A roll of individually-severeable foam plastic trayliners is additionally provided. Each trayliner is for lining a tray including a base having a multiplicity of holes, and the trayliners each have a multiplicity of holes arranged such that at least a portion of the holes of the trayliner will be generally aligned with at least a portion of the multiplicity of holes of the base of the tray.

23 Claims, 5 Drawing Sheets

OTHER PUBLICATIONS

1998, Jacobs, *Plasma Sterilization*, Advanced Sterilization Products website (3 pages).

1998, *Plasma*, Advanced Sterilization Products website (2 pages).

1997 Brochure for Instrument Trayliner, General Hospital Supply Corporation (1 page).

Brochure for Plasma–Cel Instrument Guards, Cygnus Medical (4 pages), Prior Art.

Brochure for Steri–Cel Instrument Protectors, Cygnus Medical (2 pages), Prior Art.

Brochure for Opcell Foam Plastic, Sentinel Products Corp. (1 page), Prior Art.

Brochure for Cell–Aire Polyethylene Foams, Sealed Air Corporation (1 page), Prior Art.

* cited by examiner

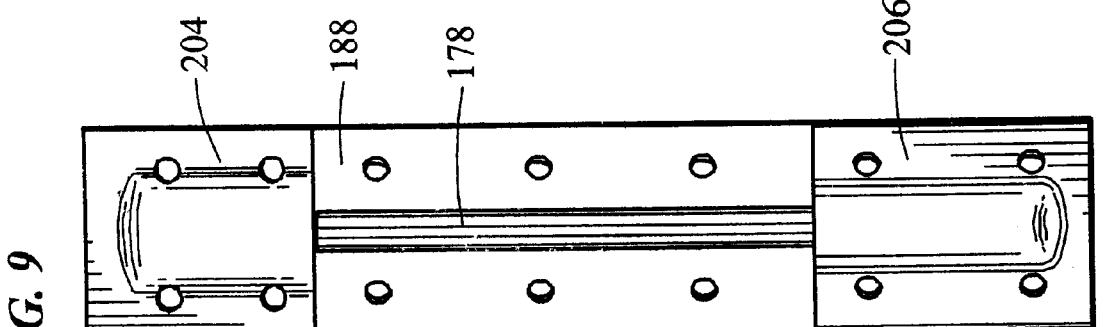

INSTRUMENT POUCH FOR STERILIZATION PROCESS AND METHOD OF STERILIZING AN ARTICLE

RELATED APPLICATIONS

This application is a continuation-in-part of U.S. patent application Ser. No. 09/148,121 filed on Sep. 4, 1998, now U.S. Pat. No. 6,248,293, the disclosures of which is herein incorporated by reference in its entirety.

BACKGROUND

The present disclosure relates, in general, to a trayliner for a sterilization process. Even more particularly, the present disclosure relates to a trayliner for cushioning articles in a low temperature hydrogen-peroxide gas plasma sterilization system. The present disclosure also relates to an instrument pouch for protecting an article, such as a surgical instrument, during a low temperature hydrogen-peroxide gas plasma sterilization process.

As is well known, articles used in the health care industry, such as surgical instruments, must be sterilized before and after each use. Many articles, such as fiber optic endoscopes, laser handpieces, power drills and ophthalmic devices, are very delicate and, thus, are preferably cushioned when being sterilized to prevent costly repairs and to reduce down time.

There are generally three sterilization processes for use on surgical equipment: high temperature steam, ethylene oxide, and low temperature hydrogen-peroxide gas plasma. For a number of well-known reasons, hydrogen-peroxide gas plasma sterilization is becoming the preferred sterilization method. For example, hydrogen-peroxide gas plasma sterilization has significantly less corrosive effect on metal surgical instruments, and leaves no residue that may cause the sterilized surgical instruments to be irritating or toxic to patients. In addition, hydrogen-peroxide gas plasma sterilization produces no toxic byproducts and requires no special ventilation or aeration. Hydrogen-peroxide gas plasma sterilization is also faster than other sterilization processes since a waiting period to allow toxic byproducts to dissipate is unnecessary.

A STERRAD® hydrogen-peroxide gas plasma sterilization system available from Advanced Sterilization Products of Irvine, Calif., for example, is designed to provide non-toxic, dry, low-temperature sterilization in about one hour, without toxic residues. However, the STERRAD® system is not usable with cellulose-based products like linen or paper normally used in other sterilization processes. Cellulose-based products, as well as many other materials commonly used in sterilization, are highly absorbent and trap fluid during the sterilization process. During hydrogen-peroxide gas plasma sterilization, absorbent materials can cause an unwanted residue to be left on the articles being sterilized. Thus, the use of such absorbent materials in the hydrogen-peroxide sterilization process requires different cycle parameters to achieve sterilization, without leaving a residue on the article being sterilized, in a fixed cycle of the current design.

The STERRAD® system includes a sterilization chamber and a tray for holding surgical instruments and articles such as fiber optic endoscopes, laser handpieces, power drills and ophthalmic devices, within the sterilization chamber during the sterilization process. The tray includes a base having a multiplicity of holes for allowing plasma to flow there through and contact the article being sterilized during the sterilization process.

One existing trayliner for use with the STERRAD® system is available from Cygnus Medical of Branford, Conn., under the trademark Plasma-Cel™ and consists of a sheet of "open cell" foam, more specifically open cell polyethylene foam. While this trayliner is not cut to the exact dimensions of the tray, the trayliner generally covers the base of the tray of the STERRAD® system to cushion surgical instruments during the sterilization process. The open cell structure of the plastic foam trayliner allows plasma to pass directly through the trayliner, such that the foam trayliner does not interfere with the passage of plasma through the tray holes. While this particular open cell foam trayliner has been found to work with the STERRAD® system, since open cell polyethylene is relatively expensive, the Plasma-Cel™ trayliner typically is reused a number of times to make each individual trayliner cost effective. Thus, users are instructed that they may reuse the Plasma-Cel™ trayliner up to five times. It is unlikely, however, that users feel comfortable with the idea of reusing, and keeping track of the number of uses of, a sterilization trayliner in a sterile hospital environment. Thus, the relatively expensive open cell polyethylene foam trayliners are often disposed of after a single use. The sheets are provided as precut individual pieces or in a roll. Cygnus Medical also provides instrument pouches under the trademark Plasma-Cel™, which are also made of "open cell" polyethylene foam. Cygnus instructs its customers to sterilize lumen devices in the Plasma-Cel™ pouches only, since such devices are not properly sterilized when used with the Plasma-Cel™ trayliners.

U.S. Pat. Nos. 4,142,632, D263,076, and D263,745 to Sandel disclose surgical instrument holders and instrument tip protector devices. However, the holders and devices disclosed by Sandel are also made of open-cell foam. In particular, the holders and devices disclosed by Sandel are made of open-cell polyurethane ester foam.

What is still needed, accordingly, is a trayliner for cushioning articles, such as fiber optic endoscopes, laser handpieces, power drills and ophthalmic devices, in a hydrogen-peroxide gas plasma sterilization system. Preferably, the trayliner will have low absorbency, yet will allow the passage of plasma there through, such that an article can effectively be sterilized in a hydrogen-peroxide gas plasma sterilization system. In addition, the trayliner will preferably be relatively inexpensive such that disposing of the trayliner after a single use is cost effective.

What is also still needed is an instrument pouch for protecting articles, such as fiber optic endoscopes, laser handpieces, power drills and ophthalmic devices, during a hydrogen-peroxide gas plasma sterilization process. Preferably, the instrument pouch will have low absorbency, yet will allow the passage of plasma there through, such that an article is protected, yet can effectively be sterilized in a hydrogen-peroxide gas plasma sterilization system. In addition, the instrument pouch will preferably be relatively inexpensive such that disposing of the instrument pouch after a single use is cost effective.

SUMMARY

Accordingly, a method for sterilizing an article in a hydrogen-peroxide gas plasma sterilization unit is provided. The method includes placing the article within a foam plastic instrument pouch having a closed cell construction, and positioning the closed cell foam plastic instrument pouch containing the article within the sterilization chamber of the sterilization unit. The hydrogen-peroxide gas plasma sterilization unit is then operated such that the article within the instrument pouch is sterilized, whereby the instrument pouch containing the article is removed from the sterilization unit. The sterilized article is left within the instrument pouch until the sterilized article is actually used.

According to an additional aspect of the present disclosure the foam plastic instrument pouch is provided with a multiplicity of holes.

According to another aspect of the present disclosure the foam plastic instrument pouch is configured with a multiplicity of holes and the instrument pouch containing the article to be sterilized is placed in a tray of the sterilization system such that at least a portion of the holes of the instrument pouch will be generally aligned with at least a portion of a multiplicity of holes of a base of the tray. The tray containing the foam plastic instrument pouch and the article is then placed within the sterilization unit.

According to another aspect of the present disclosure, the foam plastic instrument pouch is disposed of when the sterilized article is actually used.

An instrument pouch for containing and protecting an article during a sterilization process is also provided. The pouch includes a foam plastic backing sheet for lining a base of a tray, the base having a multiplicity of holes, and a foam plastic pocket secured to the backing sheet such that at least a portion of an article to be sterilized can be received between the pocket and the backing sheet. The instrument pouch has a multiplicity of holes arranged such that at least a portion of the holes of the pouch will be generally aligned with at least a portion of the multiplicity of holes of the base of the tray when the pouch is positioned on the base of the tray.

According to one aspect of the present disclosure the foam plastic of the instrument pouch has a closed cell construction.

According to another aspect of the present disclosure the backing sheet of the instrument pouch includes two spaced-apart, generally parallel slits forming a belt for receiving a portion of the article to be sterilized.

According to an additional aspect of the present disclosure the instrument pouch further includes a foam plastic strip secured to the backing sheet, forming a belt for receiving a portion of the article to be sterilized.

A roll of foam plastic trayliners is also provided by the present disclosure. Each trayliner is for lining a tray including a base having a multiplicity of holes, and the trayliners each have a multiplicity of holes arranged such that at least a portion of the holes of the trayliner will be generally aligned with at least a portion of the multiplicity of holes of the base of the tray when the trayliner is positioned on the base of the tray. The foam plastic trayliners have a closed cell construction.

According to another aspect of the present disclosure the roll includes perforations separating each trayliner such that the trayliners are individually severeable.

Still other features and advantages will become apparent upon reading the following detailed description in conjunction with the drawings and the appended claims.

BRIEF DESCRIPTION OF THE DRAWINGS

FIGS. 6–9 show various instrument pouches according to the present disclosure, with each pouch holding a ophthalmic device.

DETAILED DESCRIPTION

Figure 1:
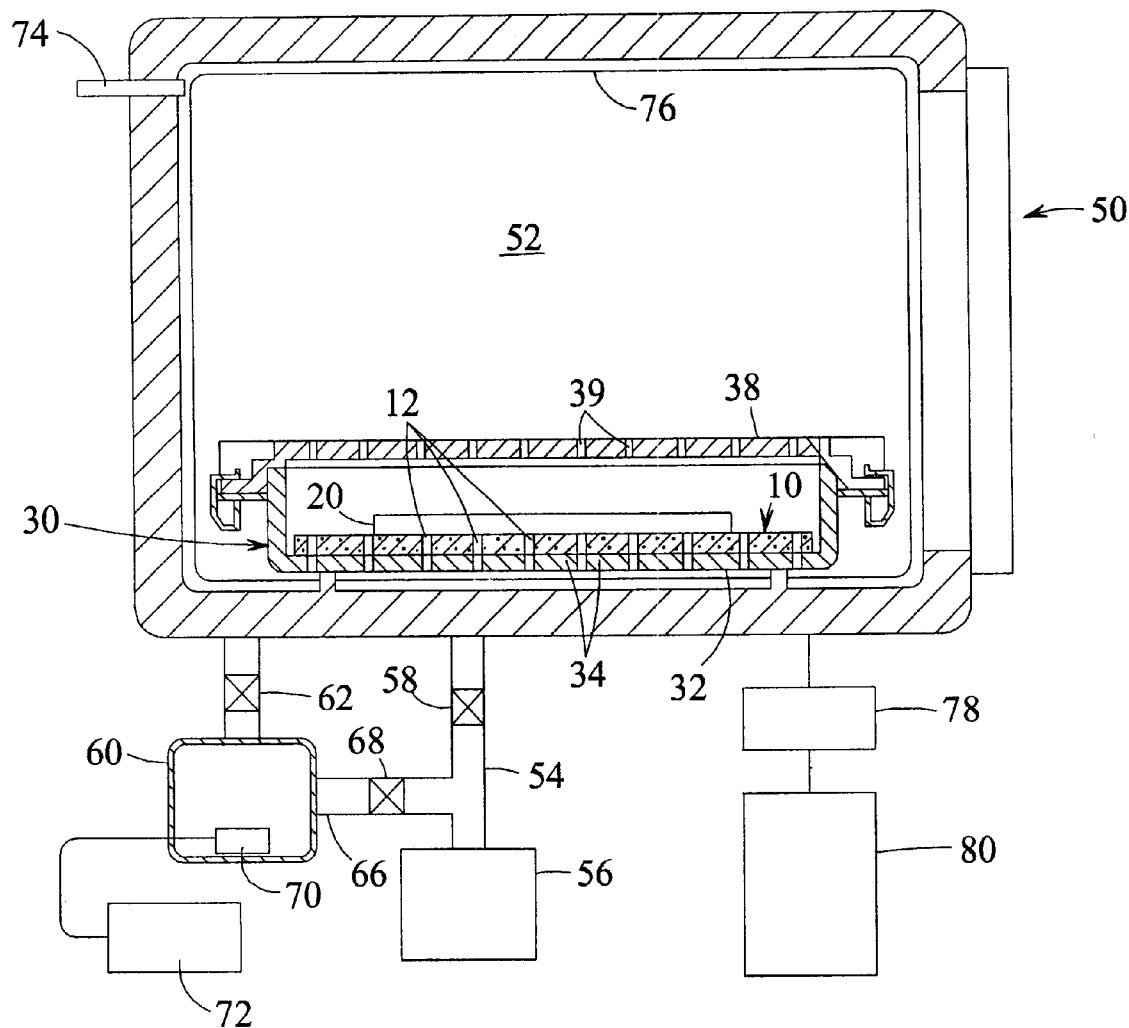
FIG. 1 shows a cross-sectional view of a trayliner cushioning a simplified representation of an article to be sterilized, such as a fiber optic endoscope, laser handpiece, power drill or ophthalmic device, in a somewhat schematic representation of a sterilization unit.
Figure 2:
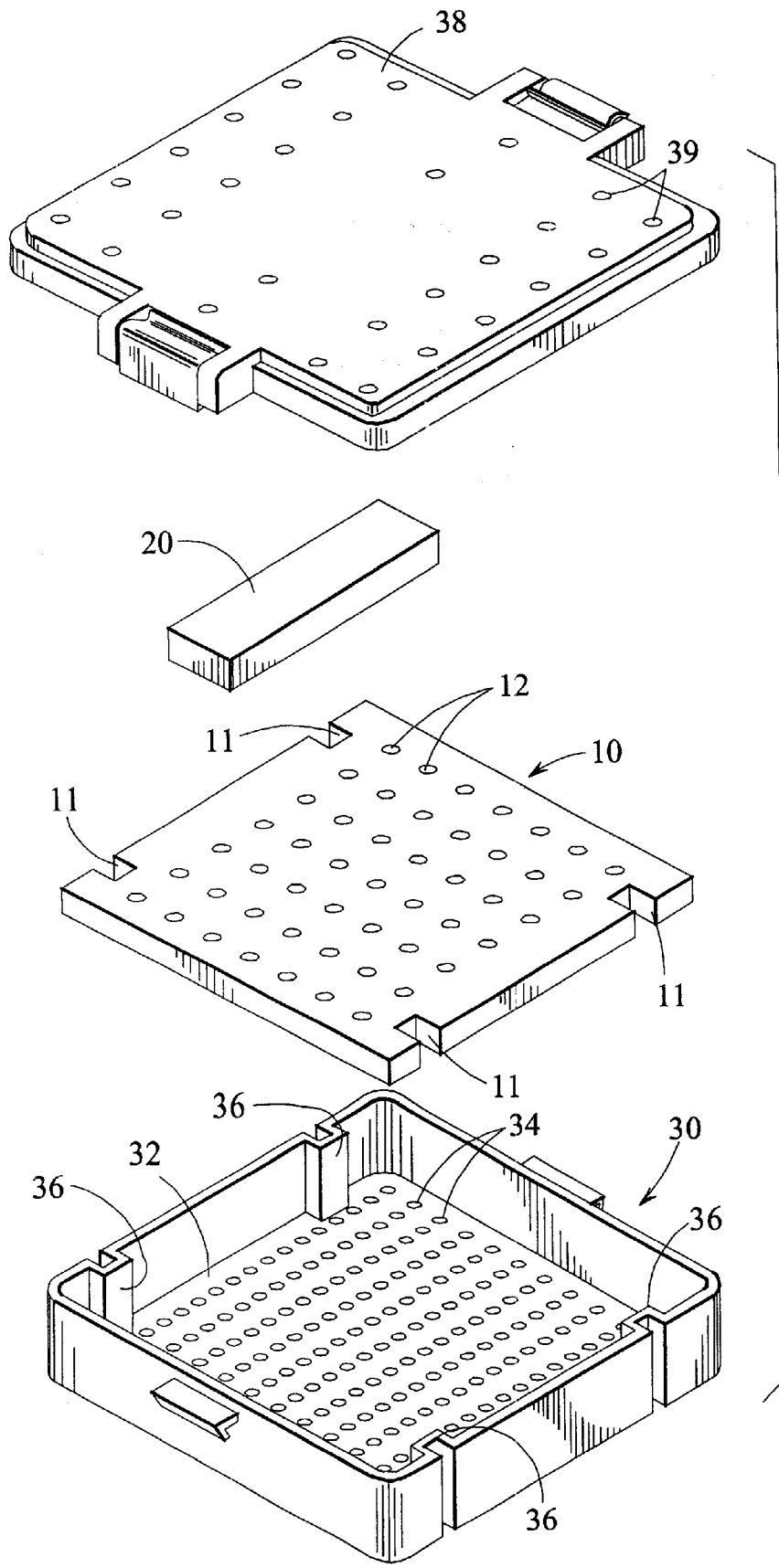
FIG. 2 shows an isometric, exploded view of a tray, the article to be sterilized and the trayliner of FIG. 1.

Referring to FIGS. 1 and 2, a trayliner 10 is provided for cushioning an article 20 to be sterilized, such as a fiber optic endoscope, laser handpiece, power drill or ophthalmic device, during a sterilization process. The trayliner 10 generally comprises a sheet of plastic foam cut to substantially cover a base 32 of a sterilization tray 30. Preferably, the trayliner 10 is cut to the exact dimensions of the base 32 and, in fact, includes notches 11 corresponding to channels 34 in a sidewall 36 of the tray 30.

The trayliner 10 also has a multiplicity of holes 12 arranged such that at least a portion of the holes of the trayliner will be generally aligned with at least a portion of a multiplicity of holes 34 in the base 32 of the sterilization tray 30. The multiplicity of holes 12 in the trayliner 10 allows for the unobstructed passage of a sterilization medium through the tray 30 and the trayliner 10. The number of holes 12 provided in the trayliner 10 may vary, but is generally enough to allow at least a sufficient amount of sterilization medium to circulate within the tray 30 for purposes of sterilization. As illustrated by the particular trayliner 10 shown, the holes 12 are circular and arranged in diagonal rows corresponding to diagonal rows of the circular holes 34 of the tray 30. Preferably, the number of holes 12 of the trayliner 10 is equal to approximately half the number of holes 32 of the tray 30, such that every other hole of the base 32 has a corresponding hole of the trayliner. The arrangement and number of holes 12 in the trayliner 10, however, is ultimately based upon the arrangement and number of holes 32 provided in the tray. As shown, the tray 30 also includes a cover 38 having a multiplicity of holes 39.

The plastic foam of the trayliner 10 preferably has a closed cell construction. A specific closed cell foam suitable for use in the practice of each embodiment of this invention is Cell-Aire® polyethylene foam available from Sealed Air Corporation of Saddle Brook, N.J. See the following Table 1 for exemplary characteristics of the Cell-Aire® product.

TABLE 1

| Physical Properties | Test Method | CA 20 | CA 30 | CA 60 | CA 90 | CA 125 | CA 185 | CA 250 |
| --- | --- | --- | --- | --- | --- | --- | --- | --- |
| Nominal Thickness | | 1/48" | 1/32" | 1/16" | 3/32" | 1/8" | 3/16" | 1/4" |
| Compressive Strength | ASTM D3575-93 | 1.4 | 2.3 | 2.5 | 2.6 | 2.8 | 2.8 | 2.9 |
| Vertical Direction (psi) | Suffix D @ 25%/50% | 8.0 | 9.5 | 9.6 | 9.8 | 10.0 | 10.4 | 9.6 |

TABLE 1-continued

| Physical Properties | Test Method | CA 20 | CA 30 | CA 60 | CA 90 | CA 125 | CA 185 | CA 250 |
|---|---|---|---|---|---|---|---|---|
| Compression Set (%) | ASTM D3575-93 Suffix B | 15.5 | 16.8 | 25.0 | 29.0 | 31.9 | 33.7 | 29.8 |
| Tensile Stress (psi) | ASTM D3575-93 | 118 | 106 | 86 | 61 | 62 | 43 | 41 |
| (@ Each Thickness) | Suffix T MD/CMD | 44 | 35 | 29 | 26 | 25 | 24 | 22 |
| Elongation (%) | ASTM D3575-93 | 6 | 8 | 8 | 13 | 18 | 13 | 21 |
|  | Suffix T MD/CMD | 2 | 3 | 3 | 3 | 8 | 5 | 8 |
| Tear Resist. (lb/in) | ASTM D3575-93 | 13.6 | 10.9 | 8.8 | 9.0 | 8.5 | 7.4 | 8.3 |
| (@ Each Thickness) | Suffix G MD/CMD | 20.3 | 18.4 | 15.0 | 14.0 | 13.6 | 11.5 | 11.9 |
| Density Range (lb/ft) | ASTM D3575-93 | 1.35–1.55 | 1.20–1.40 | 1.10–1.30 | 1.10–1.30 | 1.10–1.30 | 1.10–1.30 | 1.10–1.30 |
| Water Absorp. (lb/ft) | ASTM D3575-93 Suffix L | <0.1 | <0.1 | <0.1 | <0.1 | <0.1 | <0.1 | <0.1 |
| Thermal Stability MD/CMD | ASTM D3575-93 Suffix S | <5%** | <5%** | <5%** | <5%** | <5%** | <5%** | <5%** |
| Water Vapor Transmission Rate GM/100 in$^2$/24 hr. | ASTM F-1249 | 0.517 | 0.204 | 0.173 | 0.110 | 0.086 | 0.089 | 0.052 |
| Thermal Resistance R-Value (HR-FT$^2$-° F./BTU) | ASTM C518-91 | 6 Layers 0.77 | 6 Layers 0.90 | 5 Layers 1.03 | 1 Layer 0.47 | 1 Layer 0.53 | 1 Layer 0.89 | 1 Layer 0.86 |
| Thermal Conductivity K-Value (BTU-IN/HR-FR$^2$-° F.) | ASTM C518-91 | 6 Layers 0.20 | 6 Layers 0.23 | 5 Layers 0.25 | 1 Layer 0.19 | 1 Layer 0.21 | 1 Layer 0.25 | 1 Layer 0.29 |
| Static Decay (Anti-Static Grade) | EIA STD 541 Appendix F | N/A | <2 sec | <2 sec | <2 sec | <2 sec | <2 sec | <2 sec |
| Surface Resistivity (Anti-Static Grade) | EIA STD 541 Section 4.3 | N/A | $1.0 \times 10^9$- $1.0 \times 10^{12}$ | $1.0 \times 10^4$- $1.0 \times 10^{12}$ | $1.0 \times 10^9$- $1.0 \times 10^{12}$ | $1.0 \times 10^9$- $1.0 \times 10^{12}$ | $1.0 \times 10^8$- $1.0 \times 10^{12}$ | $1.0 \times 10^9$- $1.0 \times 10^{12}$ |
| Flexibility +71° F.-65° F. | PP-C-1752 D | Pass | Pass | Pass | Pass | Pass | Pass | Pass |
| Contact Corrosivity (Alum. Plate) | Method 3005 FED STD 101-- | None | None | None | None | None | None | None |

**Except Thickness Direction

Closed cell foam plastic provides many advantages for use in sterilization. For example, closed cell foam plastic is less likely to develop loose particulate material when cut or processed for distribution. This is important of course since loose particulate material is very undesirable within the surgical environment. Also, closed cell foam plastic is relatively easy to sterilize because closed cell foam plastic has few cracks, nooks and crannies and, thus, a sterilization medium such as hydrogen peroxide gas plasma, for example, can more easily reach all surfaces of the closed cell foam plastic and provide sterilization.

The trayliner 10 is particularly adapted for use in a hydrogen-peroxide ($H_2O_2$) gas plasma sterilization system. Advanced Sterilization Products of Irvine, Calif., for example, markets a STERRAD® $H_2O_2$ gas plasma sterilization system. Such systems are becoming increasingly popular by providing a non-toxic, dry, low temperature sterilization process.

FIG. 1 shows a schematic representation of an $H_2O_2$ gas plasma sterilization system 50. Such a system is disclosed in greater detail in U.S. Pat. No. 5,667,753, the disclosure of which is incorporated herein by reference. In general, however, the sterilization system 50 includes a sterilization chamber 52 for containing an article 20 to be sterilized.

For purposes of simplification and generalization, the article 20 to be sterilized is illustrated as a rectangular block. However, it should be understood that the article 20 can comprise any medical device requiring sterilization before and after each use, and, in particular, delicate surgical devices, such as fiber optic endoscopes, laser handpieces, power drills and ophthalmic devices, that are preferably cushioned when being sterilized to prevent costly repairs and to reduce down time.

The chamber 52 of the sterilization system 50 includes an outlet 54 leading to a vacuum pump 56 for evacuation of the chamber. The outlet 54 includes a valve 58 for isolating the chamber 52 from the pump 56. The chamber 52 also includes an inlet 60, containing a valve 62, that is connected to an enclosure 64 containing hydrogen peroxide. A conduit 66 having a valve 68 connects the $H_2O_2$ enclosure 64 to the vacuum pump 56. The enclosure 64 contains a heater 70 attached to a temperature controller 72, while the chamber 52 includes a peroxide monitor 74. The chamber 52 also includes a radio frequency (RF) electrode 76, to which is attached a matching network 78 and an RF power supply 80.

Operation of the $H_2O_2$ gas plasma sterilization system 50 includes opening valve 62 to allow $H_2O_2$ vapor from the enclosure 64 to be delivered into the chamber 52. The $H_2O_2$ may be heated by the heater 70 in the enclosure 64 to facilitate the release of the $H_2O_2$ vapor. Air or inert gas may also be added to the $H_2O_2$ vapor. The article 20 to be sterilized is either treated with peroxide vapor until sterilized or pretreated with peroxide vapor in the chamber 52 before plasma with sufficient power to sterilize is generated.

The chamber 52 may then be evacuated to facilitate generation of the plasma. The article 20 is subject to a plasma by applying power from the RF power supply 80 to the RF electrode 76. The article 20 remains in the plasma for a period sufficient to effect complete sterilization and/or to remove residual $H_2O_2$.

The term "plasma" is intended to include any portion of the gas or vapor that contains electrons, ions, free radicals, dissociated and/or excited atoms or molecules produced as a result of an applied electric field, including any accompanying radiation that might be produced.

A preferred method for sterilizing an article 20 includes positioning the closed cell foam plastic trayliner 10 having the multiplicity of holes 12 into the tray 30, as shown in FIG. 2, and positioning the article 20 on the trayliner. The tray 30 containing the trayliner 10 and the article 20 is then placed in the sterilization unit 50, as shown in FIG. 1, and the sterilization unit is operated as the unit normally would be until the article is sterilized.

The method may further include arranging the multiplicity of holes 12 in the foam plastic trayliner 10 such that, at least a portion of the holes of the trayliner will be generally aligned with at least a portion of the multiplicity of holes 34 of the base 32 of the tray 30. The foam plastic trayliner 10 is then positioned on the base 32 of the tray 30 such that at least a portion of the holes 12 of the trayliner are generally aligned with at least a portion the holes 34 of the base, as shown in FIGS. 1 and 2, whereby the trayliner does not interfere with the passage of the sterilization medium through the holes of the tray. Preferably, the number of holes 12 of the trayliner 10 equals approximately half the number of holes 32 of the tray 30, such that the holes of the trayliner correspond to every other hole of the tray.

The method may also include removing the tray 30 from the sterilization unit 50, after the sterilization unit has finished a normal sterilization cycle, and removing the then sterilized article 20 from the tray. The foam plastic trayliner 10 is then preferably disposed of in a proper waste container after the single sterilization process.

Figure 3:
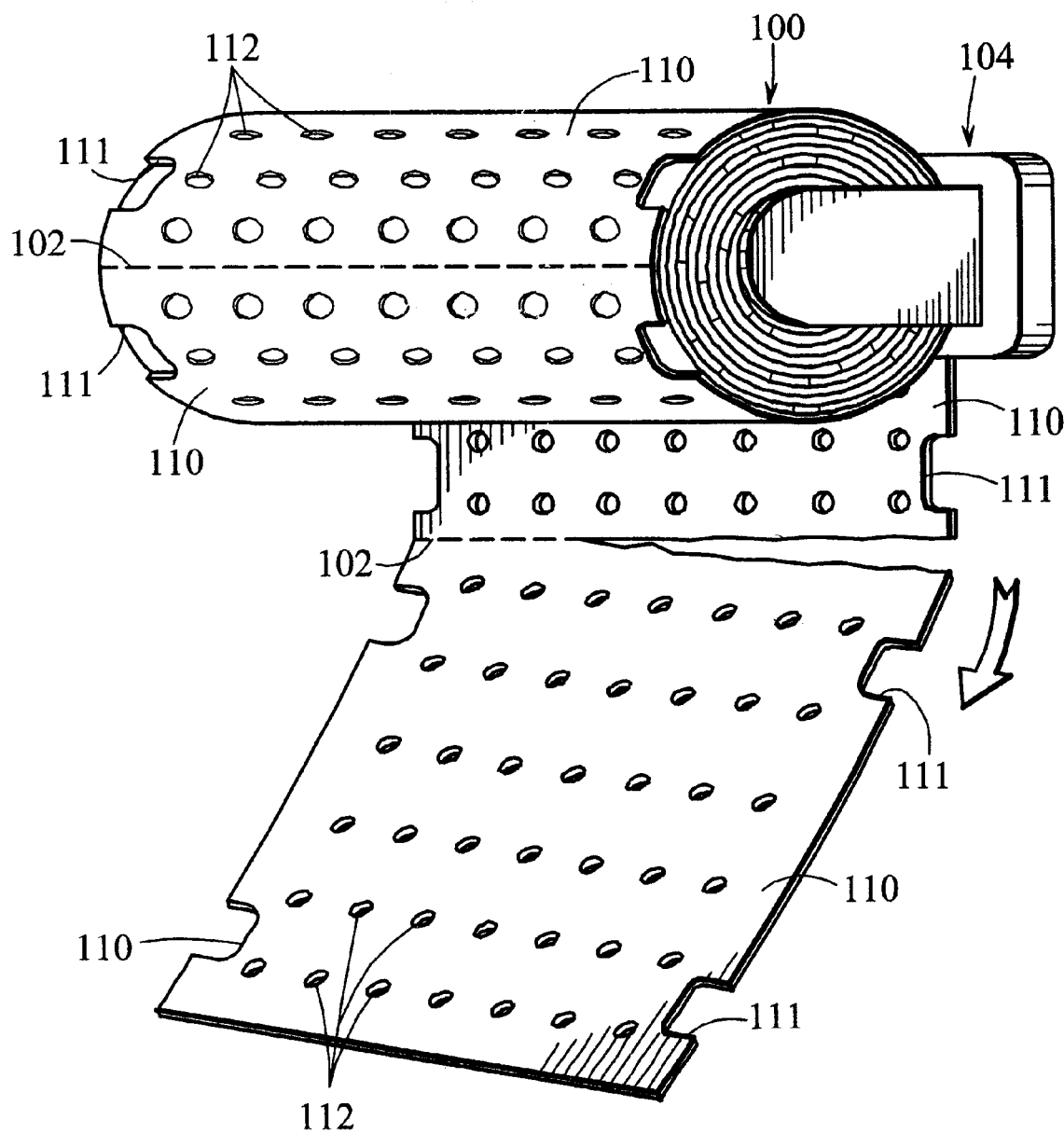
FIG. 3 shows an isometric view of a roll of individually severeable trayliners and a method of dispensing the severeable trayliners according to the present disclosure.

Referring to FIG. 3, foam plastic trayliners 110 according to the present disclosure can be dispensed from a roll 100. Preferably, the trayliners 110 are individually-severeable such that the trayliners can be separated from each other by perforations 102 that allow individual sheets to be easily torn from the roll 100, as shown in FIG. 3. It should be understood, however, that a non-perforated roll of trayliners could be provided and cut to size by a user with a pair of scissors, for example. As also shown, the roll 100 can be simply mounted within a typical paper towel dispenser 104. The paper towel dispenser 104 is preferably mounted next to a sterilization system 50 for convenient access to the trayliners 110.

Preferably, each trayliner 110 is sized to the exact dimensions of the base 32 and, in fact, includes notches 111 corresponding to channels 34 in a sidewall 36 of the tray 30. The trayliners 110 also have a multiplicity of holes 112 arranged such that at least a portion of the holes of the trayliner will be generally aligned with at least a portion of a multiplicity of holes 34 in the base 32 of the sterilization tray 30. The plastic foam of the trayliners 110 preferably has a closed cell construction. A specific closed cell foam suitable for use is Cell-Aire® polyethylene foam.

Figure 4:
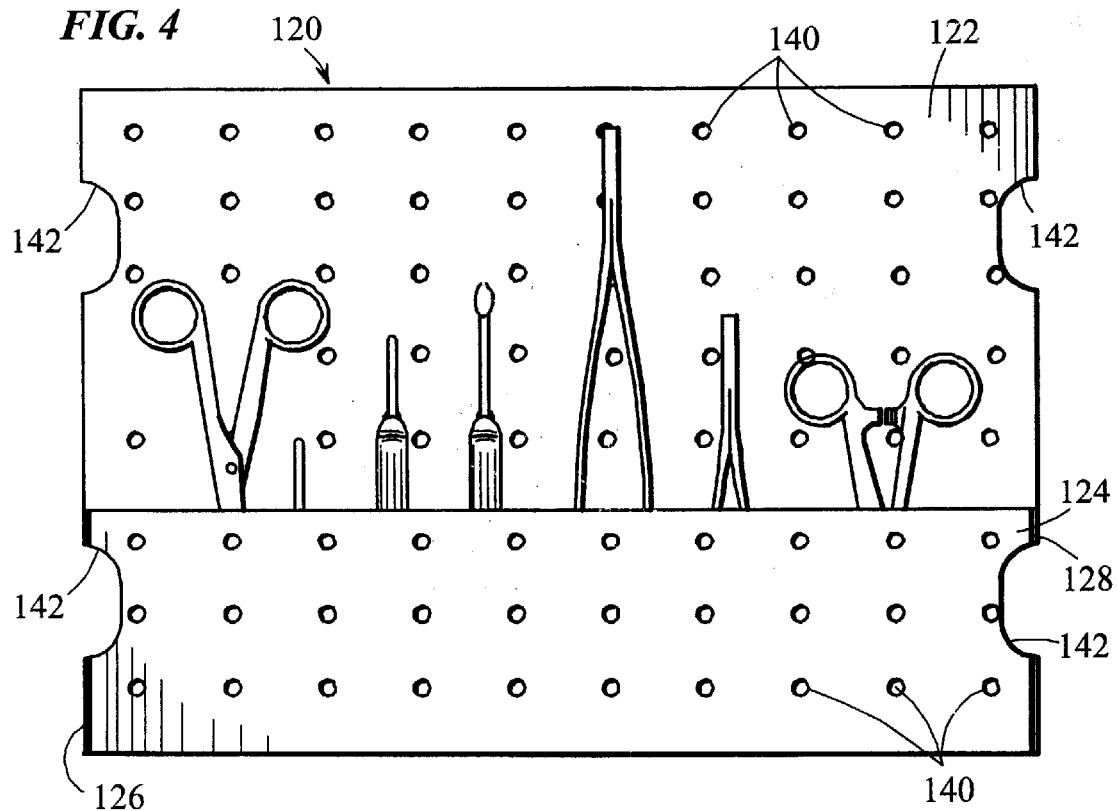
FIG. 4 shows an instrument pouch according to the present disclosure containing miscellaneous surgical instruments.

An instrument pouch 120 for containing an article in the tray 30 of the hydrogen-peroxide gas plasma sterilization unit 50, such that the article is cushioned, is also provided by the present disclosure, as shown in FIG. 4. The instrument pouch 120 is made of closed-cell foam plastic and includes a backing sheet 122 for cushioning the article. The sheet 122 is preferably provided in substantially the same size and shape as the base 32 of the tray 30. A pocket 124 is secured to the sheet 122 such that at least a portion of an article to be sterilized can be received between the pocket and the sheet. Preferably, the pocket 124 is unitary with the backing sheet 122 and folded over the backing sheet, with side edges 126, 128 of the pocket being secured to the backing sheet. The side edges 126, 128 are preferably secured to the backing sheet 124 by heating and applying pressure such that the side edges are bonded to the backing sheet 122. Thus, the instrument pouch 120 includes a single large pocket, which can contain a plurality of articles, such as surgical instruments like scissors, tweezers and scalpels. Articles that have been sterilized within the instrument pouch 120, can be left in the instrument pouch, after the sterilization process, until the sterilized article is actually used. Then, the instrument pouch 120 is preferably disposed of.

The instrument pouch 120 has a multiplicity of holes 140 arranged such that at least a portion of the holes of the instrument pouch will be generally aligned with at least a portion of the multiplicity of holes 34 of the base 33 of the tray 30 when the instrument pouch is positioned on the base of the tray, whereby hydrogen-peroxide vapor and plasma will be allowed to pass through the tray and the instrument pouch to sterilize the article, and liquid hydrogen-peroxide will be allowed to drain from the tray. The holes 140 pass through both the backing sheet 122 and the pocket 124. The instrument pouch 120 includes notches 142 corresponding to the channels 34 in the sidewall 36 of the tray 30.

Figure 5:
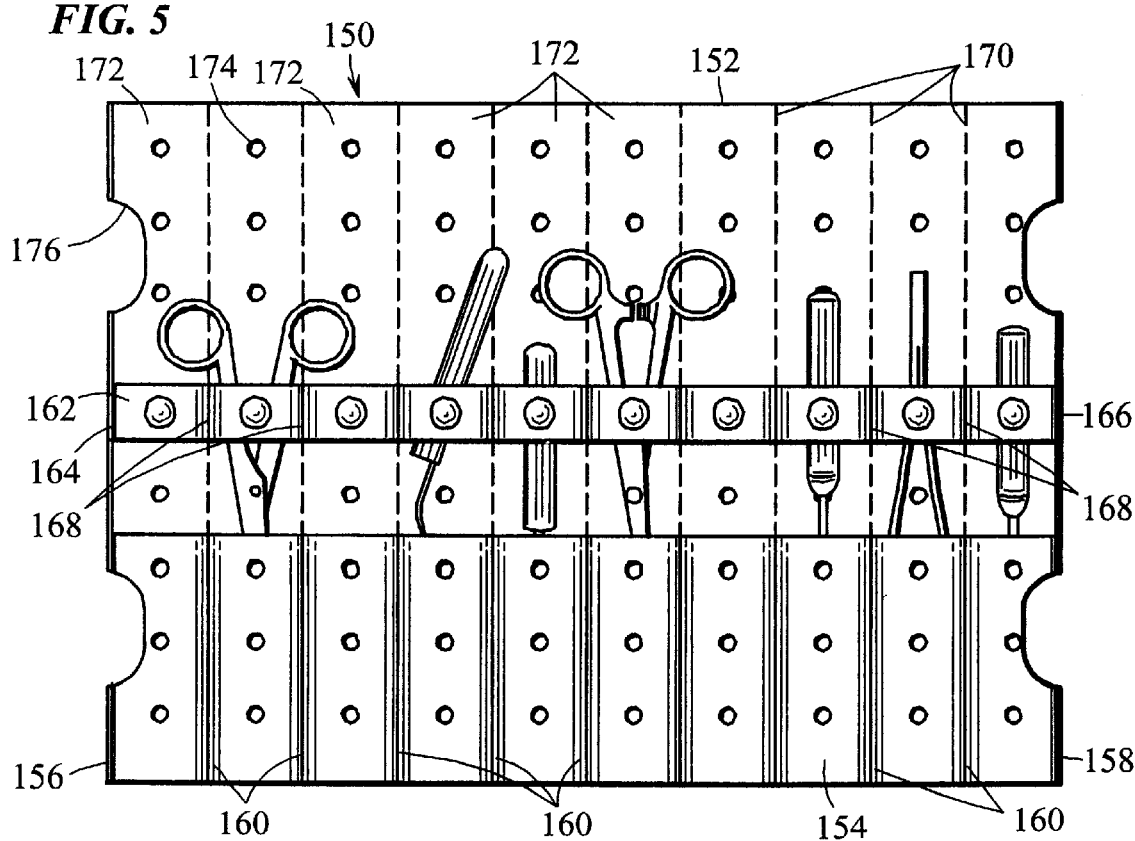
FIG. 5 shows a sheet of individually-severeable instrument pouches according to the present disclosure containing miscellaneous surgical instruments.

Another closed-cell foam plastic instrument pouch 150 is shown in FIG. 5. The instrument pouch 150 includes a backing sheet 152, preferably provided in substantially the same size and shape as the base 32 of the tray 30, and a pocket 154 secured to the sheet. The pocket 154 is unitary with the backing sheet 152 and folded over the backing sheet, with side edges 156, 158 of the pocket being secured to the backing sheet. The pocket 154 is also secured to the sheet at equally spaced-apart intervals 160 parallel with and between the side edges 156, 158. Thus, the instrument pouch 150 includes a plurality of small pockets, each for containing a single article, as shown. The pouch 150 also includes a closed cell foam plastic strip 162 secured to the backing sheet 152 and spaced from the pocket 154. The strip 162 is secured at its ends 164, 166 and at equally spaced intervals 168 between the ends, such that it acts as a belt for securing the articles. The instrument pouch 150 can also include perforations 170 aligned with the intervals 168 of the strip 162 and the intervals 160 of the pocket 154, such that individual article pouches 172 can be torn from the larger instrument pouch. The instrument pouch 150 also has a multiplicity of holes 174 and notches 176 similar the pouch 120 of FIG. 5.

FIGS. 6–9 show various closed-cell foam plastic instrument pouches 180, 182, 184, 186 according to the present disclosure, with each pouch holding an article, such as an ophthalmic device 178. Each instrument pouch includes a backing sheet 188. The instrument pouch 180 of FIG. 6 simply includes a relatively large pocket 190, while the instrument pouch 182 of FIG. 7 includes a relatively smaller pocket 192 and a belt 194 spaced from the pocket. The belt 194 is formed from a strip of closed cell foam plastic secured to the backing sheet 188. The instrument pouch 184 of FIG. 8 includes a pocket 196 and a belt 198 spaced from the pocket. The belt 198 is formed from two parallel spaced slits 200, 202 provided in the backing sheet 188. The instrument pouch 186 of FIG. 9 includes pockets 204, 206 secured to both ends of the backing sheet 188. Thus, instrument pouches according to the present invention can be provided in various shapes, sizes and configurations.

The principles, preferred embodiments and modes of operation of the present trayliners and instrument pouches have been described in the foregoing specification. The presently disclosed trayliners and instrument pouches, however, are not to be construed as limited to the particular embodiments shown as these embodiments are regarded as illustrious rather than restrictive. Moreover, variations and changes may be made by those skilled in the art without departing from the spirit of the presently disclosed trayliners and instrument pouches as set forth by the following claims.

What is claimed is:

1. A method for sterilizing an article in a hydrogen-peroxide gas plasma sterilization unit wherein the article is treated within a sterilization chamber of the unit with a hydrogen-peroxide vapor, the method comprising:

placing the article within an instrument pouch fabricated from a closed cell, foam material, the closed cell material having a percent elongation as determined under ASTM D3575-93 that is within the range of between about two percent and about twenty-one percent;

positioning the instrument pouch containing the article within the sterilization chamber of the sterilization unit;

operating the sterilization unit such that the article within the instrument pouch is sterilized;

removing the instrument pouch containing the article from the sterilization unit; and leaving the sterilized article within the instrument pouch until the sterilized article is actually used.

2. The method of claim 1 wherein the closed cell, foam material has a compression strength as determined under ASTM D3575-93 that is within the range of between about 1.4 psi at twenty-five percent deflection and about 2.9 psi at twenty-five percent deflection.

3. The method of claim 1 wherein the closed cell foam material of the instrument pouch has a compression strength as determined under ASTM D3575-93 that is within the range of between about 8 psi at fifty percent deflection and about 10.4 psi at fifty percent deflection.

4. The method of claim 1 wherein the instrument pouch comprises a multiplicity of apertures.

5. The method of claim 1 wherein the sterilization unit includes a tray with a base having a multiplicity of apertures, the method further comprising:

configuring the instrument pouch with a multiplicity of apertures;

placing the instrument pouch containing the article to be sterilized in the tray such that at least a portion of the apertures of the instrument pouch generally will be aligned with at least a portion of the multiplicity of apertures of the base of the tray; and positioning the tray containing the instrument pouch and the article within the sterilization unit.

6. The method of claim 1 further comprising disposing of the instrument pouch after use of the sterilized article.

7. A method of sterilizing an article comprising:

providing an instrument pouch fabricated from a closed cell, foam material, the closed cell, foam material having a material density as determined under ASTM D3575-93 that is within the range of between about 1.10 pounds per cubic foot and about 1.55 pounds per cubic foot;

providing a multiplicity of apertures in the instrument pouch for allowing a sterilizing medium to pass there through;

positioning the article to be sterilized within the instrument pouch;

positioning the instrument pouch containing the article in a sterilization unit; and operating the sterilization unit for a sufficient period to sterilize the article.

8. The method of claim 7 wherein the sterilization unit comprises a hydrogen-peroxide gas plasma sterilization unit that includes a tray with a base having a multiplicity of apertures, the method further comprising:

placing the instrument pouch containing the article to be sterilized in the tray such that at least a portion of the apertures of the instrument pouch will be generally aligned with at least a portion of the multiplicity of apertures of the base of the tray; and positioning the tray containing the instrument pouch and the article within the sterilization unit.

9. The method of claim 8 further comprising:

removing the tray from the sterilization unit after the article has been sterilized;

removing the instrument pouch containing the sterilized article from the tray;

leaving the sterilized article within the instrument pouch until the sterilized article is used; and disposing of the instrument pouch after use of the sterilized article.

10. An instrument pouch for containing and protecting an article during a sterilization process, the pouch comprising:

a backing sheet for lining a tray, the backing sheet being fabricated from a closed cell, foam material having a percent elongation as determined under ASTM D3575-93 that is within the range of between about two percent and about twenty-one percent and the tray including a base having a multiplicity of apertures;

a pocket secured to the backing sheet such that at least a portion of an article to be sterilized can be received between the pocket and the backing sheet, the pocket being fabricated from a closed cell, foam material having a percent elongation as determined under ASTM D3575-93 that is within the range of between about two percent and about twenty-one percent;

the instrument pouch having a multiplicity of apertures arranged such that at least a portion of the apertures of the pouch will be generally aligned with at least a portion of the multiplicity of apertures of the base of the tray when the pouch is positioned on the base of the tray.

11. The instrument pouch of claim 10 wherein the closed cell, foam material has a compression strength as determined under ASTM D3575-93 that is within the range of between about 1.4 psi at twenty-five percent deflection and about 2.9 psi at twenty-five percent deflection.

12. The instrument pouch of claim 10 wherein the closed cell, foam material has a compression strength as determined under ASTM D3575-93 that is within the range of between about 8 psi at fifty percent deflection and about 10.4 psi at fifty percent deflection.

13. The instrument pouch of claim 10 wherein the backing sheet includes two spaced apart, generally parallel slits forming a belt for receiving a portion of the article to be sterilized.

14. The instrument pouch of claim 10 further including a strip fabricated from a closed cell, foam material and being secured to the backing sheet, forming a belt for receiving a portion of the article to be sterilized.

15. An instrument pouch for lining a tray of a hydrogen-peroxide gas plasma sterilization unit such that an article contained in the tray is cushioned, the tray including a base having a multiplicity of apertures for allowing hydrogen-peroxide vapor and plasma to pass there through to sterilize the article and allowing liquid hydrogen-peroxide to drain therefrom, the instrument pouch comprising:

a backing sheet fabricated from a closed cell, foam material having a density as determined under ASTM D3575-93 that is within the range of between about 1.10 pounds per cubic foot and about 1.55 pounds per cubic foot for cushioning the article, the sheet being provided in substantially the same size and shape as the base of the tray;

a pocket composed of a closed cell, foam material and being secured to the sheet such that at least a portion of an article to be sterilized can be received between the pocket and the sheet;

the instrument pouch having a multiplicity of apertures arranged such that at least a portion of the apertures of the instrument pouch will be generally aligned with at least a portion of the multiplicity of apertures of the base of the tray when the instrument pouch is positioned on the base of the tray, whereby hydrogen-peroxide vapor and plasma will be allowed to pass through the tray and the instrument pouch to sterilize the article and liquid hydrogen-peroxide will be allowed to drain from the tray.

16. The instrument pouch of claim 15 wherein the closed cell, foam material has a compression strength as determined under ASTM D3575-93 that is within the range of between about 1.4 psi at twenty-five percent deflection and about 2.9 psi at twenty-five percent deflection.

17. The instrument pouch of claim 15 wherein the closed cell, foam material has a compression strength as determined under ASTM D3575-93 that is within the range of between about 8 psi at fifty percent deflection and about 10.4 psi at fifty percent deflection.

18. A roll of trayliners, each trayliner for lining a tray including a base having a multiplicity of apertures, the trayliners each having a multiplicity of apertures arranged such that at least a portion of the apertures of the trayliner will be generally aligned with at least a portion of the multiplicity of apertures of the base of the tray when the trayliner is positioned on the base of the tray, and wherein the trayliners are fabricated from a closed cell, foam material having a percent elongation as determined under ASTM D3575-93 that is within the range of between about two percent and about twenty-one percent.

19. The roll of trayliners of claim 18 wherein the roll includes perforations separating each trayliner such that the trayliners are individually severeable.

20. The roll of trayliners of claim 18 wherein the closed cell, foam material has a compression strength as determined under ASTM D3575-93 that is within the range of between about 8 psi at fifty percent deflection and about 10.4 psi at fifty percent deflection.

21. A roll of trayliners for lining a tray of a hydrogen-peroxide gas plasma sterilization unit such that an article contained in the tray is cushioned, the tray including a base having a multiplicity of apertures for allowing hydrogen-peroxide vapor and plasma to pass there through to sterilize the article and allowing liquid hydrogen-peroxide to drain therefrom, wherein the roll includes perforations separating each trayliner such that the trayliners are individually severeable, each individually-severeable trayliner comprising:

a sheet fabricated from a closed cell, foam material having a density as determined under ASTM D3575-93 that is within the range of between about 1.10 pounds per cubic foot and about 1.55 pounds per cubic foot for cushioning the article, the sheet being provided in substantially the same size and shape as the base of the tray;

the sheet having a multiplicity of apertures arranged such that at least a portion of the apertures of the trayliner will be generally aligned with at least a portion of the multiplicity of apertures of the base of the tray when the trayliner is positioned on the base of the tray, whereby hydrogen-peroxide vapor and plasma will be allowed to pass through the tray and the trayliner to sterilize the article and liquid hydrogen-peroxide is allowed to drain from the tray.

22. The roll of trayliners of claim 21 wherein the closed cell, foam material has a compression strength as determined under ASTM D3575-93 that is within the range of between about 1.4 psi at twenty-five percent deflection and about 2.9 psi at twenty-five percent deflection.

23. The roll of trayliners of claim 21 wherein the closed cell, foam material has a compression strength as determined under ASTM D3575-93 that is within the range of between about 8 psi at fifty percent deflection and about 10.4 psi at fifty percent deflection.

* * * * *